United States Patent [19]

Sugimori et al.

[11] Patent Number: 4,603,018
[45] Date of Patent: Jul. 29, 1986

[54] 2-CYANO-4-HALOGENOPHENYL ESTERS

[75] Inventors: Shigeru Sugimori, Fujisawashi; Toyoshiro Isoyama, Yokohamashi; Tetsuhiko Kojima, Yokohamashi; Yasuyuki Goto, Yokohamashi, all of Japan

[73] Assignee: Chisso Corporation, Osaka, Japan

[21] Appl. No.: 530,786

[22] Filed: Sep. 9, 1983

[30] Foreign Application Priority Data

| Sep. 27, 1982 | [JP] | Japan | 57-168174 |
|---|---|---|---|
| Nov. 19, 1982 | [JP] | Japan | 57-203492 |
| Jan. 22, 1983 | [JP] | Japan | 58-8896 |
| Jan. 24, 1983 | [JP] | Japan | 58-9646 |
| Mar. 2, 1983 | [JP] | Japan | 58-34224 |
| Mar. 16, 1983 | [JP] | Japan | 58-43596 |
| Apr. 9, 1983 | [JP] | Japan | 58-62417 |
| Jun. 1, 1983 | [JP] | Japan | 58-97284 |

[51] Int. Cl.$^4$ .................. C07C 121/60; C09K 3/34
[52] U.S. Cl. .................. 558/414; 252/299.63; 252/299.5
[58] Field of Search .................. 260/465 D

[56] References Cited

U.S. PATENT DOCUMENTS

| 4,198,312 | 4/1980 | Sato et al. | 260/465 D |
| 4,340,498 | 7/1982 | Sugimori | 252/299.5 |
| 4,502,974 | 3/1985 | Sugimori et al. | 252/299.63 |

FOREIGN PATENT DOCUMENTS

| 3001423 | 8/1980 | Fed. Rep. of Germany . |
| 2072214 | 9/1981 | United Kingdom . |

Primary Examiner—Nicky Chan
Attorney, Agent, or Firm—Fred Philpitt

[57] ABSTRACT

New compounds useful as constituents of liquid crystal compositions exhibiting a negative dielectric anisotropy are provided, which are 2-cyano-4-halogenophenyl esters expressed by the general formula

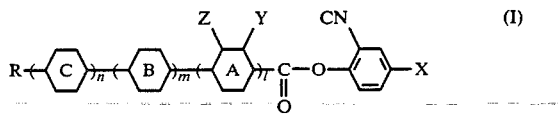

wherein R represents hydrogen atom or an alkyl group or an alkoxy group of 1 to 10 carbon atoms;

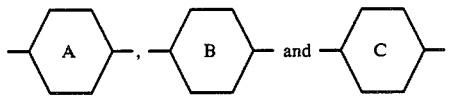

each represent either one of

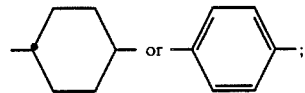

l, m and n each represent 0 or 1 and the total of l+m+n is 1, 2 or 3; X represents F or Cl; and Y and Z each represent hydrogen atom or F or Cl.

1 Claim, No Drawings

2-CYANO-4-HALOGENOPHENYL ESTERS

BACKGROUND OF THE INVENTION

1. Field of the Invention

This invention relates to novel 2-cyano-4-halogenophenyl esters as well as liquid crystal compositions containing the above-mentioned compounds and exhibiting a negative dielectric anisotropy.

2. Description of the Prior Art

Liquid crystal display elements utilize optical anisotropy and dielectric anisotropy of liquid crystal substances, and are classified into various types such as TN (twisted, nematic) type, DS (dynamic scattering) type, guest-host type, DAP type, according to their display modes, and the properties of liquid crystal substances required for their respective uses are different. Anyhow, however, in any mode, liquid crystal substances are necessary to be stable to heat, air, light, etc. and also are desirable to exhibit a liquid crystal phase in temperature ranges as broad as possible, around room temperature. At present, however, no single compound which alone satisfies such conditions is present, and it is the present status that several kinds of liquid crystal compounds or these compounds and compounds which themselves are non-liquid crystalline but, when combined with liquid crystal compounds, can form a liquid crystal composition, have been blended and the resulting liquid crystal compositions have been used.

Recently, guest-host type liquid crystal display elements as a mode of color liquid crystal display method have come to be particularly noted. For the elements, mixtures of liquid crystals and dyestuffs are used, and for positive type guest-host type display elements, liquid crystals having a negative dielectric anisotropy are used. Thus, as the constituents of such liquid crystals, liquid crystal compounds which have various specific properties, a good compatibility and a negative dielectric anisotropy have been required. The present inventors have made studies for obtaining compounds satisfying such requirement.

The object of the present invention is to provide novel compounds which are useful as constituents of liquid crystal compositions exhibiting a negative dielectric anisotropy.

SUMMARY OF THE INVENTION

The present invention resides in
2-cyano-4-halogenophenyl esters expressed by the general formula

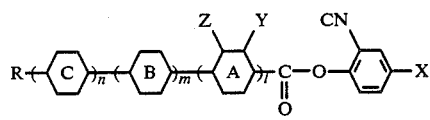

wherein R represents hydrogen atom or an alkyl group or an alkoxy group of 1 to 10 carbon atoms;

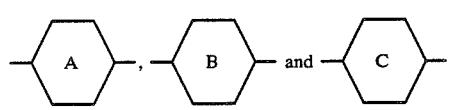

each represent either one of

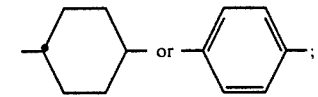

l, m and n each represent 0 or 1 and the total of l+m+n is 1, 2 or 3; X represents F or Cl; and Y and Z each represent hydrogen atom or F or Cl, and liquid crystal compositions containing at least one member of the same.

The compounds of the formula (I) are concretely classified into the following four types:
compounds expressed by the general formula

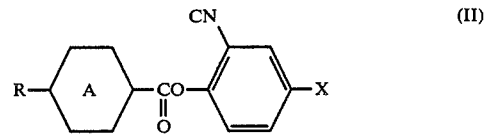

wherein R,

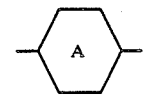

and X each are as defined above;
compounds expressed by the general formula

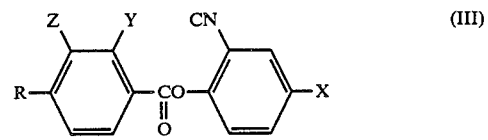

wherein R, X, Y and Z each are as defined above;
compounds expressed by the general formula

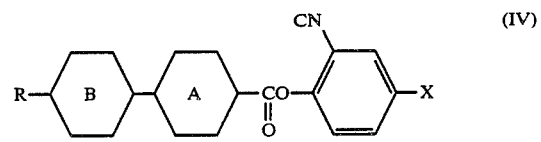

wherein R,

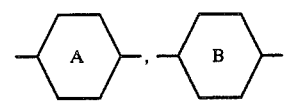

and X each are as defined above; and
compounds expressed by the general formula

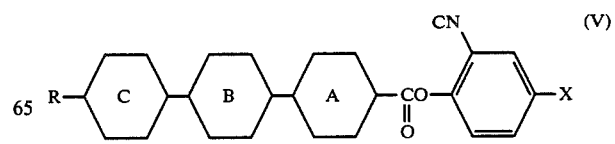

wherein R,

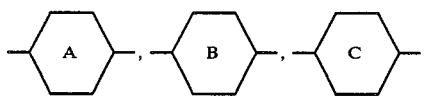

and X each are as defined above.

DETAILED DESCRIPTION OF THE INVENTION

Among the above compounds, those of the formulas (IV) and (V) are liquid crystal compounds exhibiting a nematic liquid phase up to considerably high temperatures, and have a dielectric anisotropy value of about −4, whereas compounds of the formulas (II) and (III) do not exhibit any liquid crystal phase, but, when blended with liquid crystal compounds, exhibit the same effectiveness. The above-mentioned compounds of the formulas (IV), (V), (II) and (III) are stable to heat, light, moisture, air, etc., and when they are blended with other nematic liquid crystals such as those of cyclohexanecarboxylic acid phenyl ester group, benzoic acid phenyl ester group, phenylmetadioxane group, phenylpyrimidine group, etc., it is possible to obtain liquid crystal compositions having a negative dielectric anisotropy and usable for guest-host type display elements. Further they are usable as an additive to liquid crystal compositions for two-frequency addressing scheme as well as multiplex drive which have recently been noted.

Next, preparation of the compounds of the present invention will be described. Basically, a 2-cyano-4-halogenophenol is reacted with a carboxylic acid chloride corresponding to the final objective product in the presence of pyridine to obtain an objective compound. The 2-cyano-4-halogenophenol is prepared by dehydrating the oxime of a 5-halogenosalicylaldehyde with acetic acid anhydride. This is shown by the following equation:

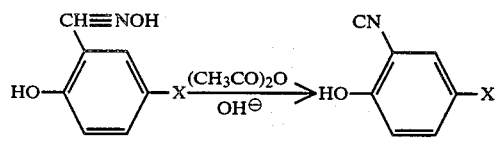

On the other hand, as to the carboxylic acids, known ones may be used for those having one ring or two rings. As to the carboxylic acids having three rings, the following (A), (C) and (E) are known, and when they are reduced with metallic sodium in isoamyl alcohol, those having three rings, (B), (D) and (F) listed on the right side are obtained.

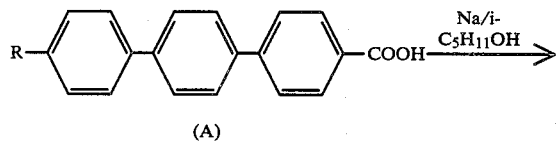

(A)

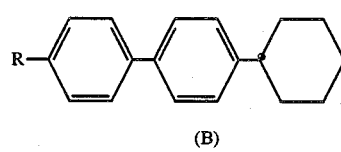

(B)

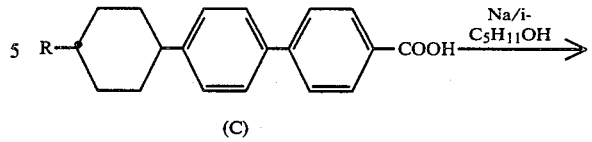

(C)

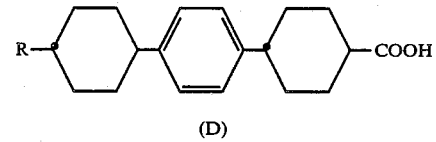

(D)

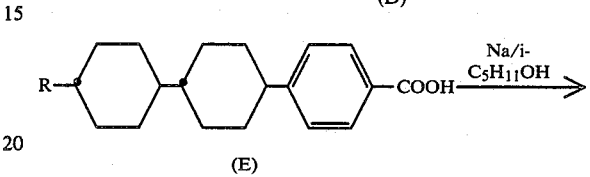

(E)

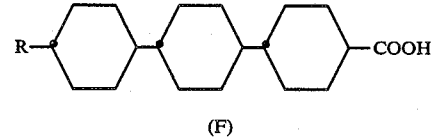

(F)

These carboxylic acids are converted in a conventional manner into the corresponding acid chlorides, which are then reacted with a 2-cyano-4-substituted phenol in the presence of pyridine to obtain the compounds of the formula (I). These reactions are illustrated by the following chemical equations:

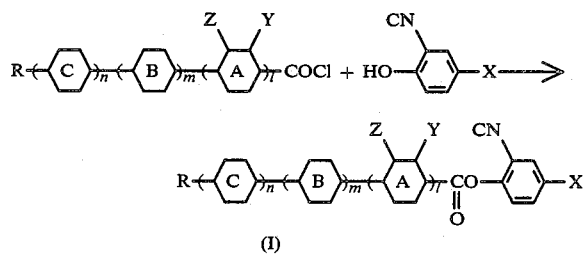

(I)

The compounds of the present invention will be further described in detail by way of Examples.

EXAMPLE 1

Preparation of trans-4-(trans-4-propylcyclohexyl)cyclohexanecarboxylic acid-2-cyano-4-fluorophenyl ester (a compound of the formula (IV) wherein R is $C_3H_7$

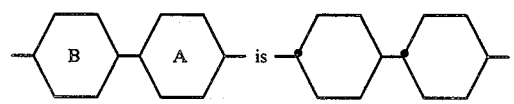

and X is F)

(1) Preparation of 2-cyano-4-fluorophenol

5-Fluorosalicylaldehyde oxime (20.2 g, 0.13 mol) was dissolved in acetic anhydride (100 ml) and refluxed for 5 hours. After completion of the reaction, acetic anhydride was distilled off under reduced pressure, followed by adding to the remaining oily substance, a solution of KOH (20 g) dissolved in water (100 ml) and ethanol (100 ml), warming the mixture at 80° C. for 2 hours, allowing it to cool down to room temperature, adding 6N hydrochloric acid (50 ml) and water (200 ml) to deposit crystals, which were then filtered off and recrystallized from methanol (30 ml) to obtain needle crystals (15.6 g) having a melting point of 121°–122° C.

(2) Esterification

2-Cyano-4-fluorophenol (1.5 g, 0.011 mol) obtained in the step (1) was dissolved in dried pyridine (20 ml), and to the resulting solution was added a solution obtained by dissolving trans-4-(trans-4'-propylcyclohexyl)cyclohexanecarboxylic acid chloride (3.0 g, 0.011 mol) in dry toluene (20 ml), followed by reaction at 60° C. for 3 hours. After completion of the reaction, the reaction product was poured in water (100 ml), followed by separating the toluene layer, washing with 6N hydrochloric acid, 2N NaOH solution and then with water, drying the toluene layer over anhydrous sodium sulfate, distilling off toluene and recrystallizing the remaining crystals from ethyl acetate (10 ml) to obtain the objective trans-4-(trans-4'-propylcyclohexyl)cyclohexanecarboxylic acid-2-cyano-4-fluorophenyl ester (2.7 g, yield 68%). C-N point: 108.7° C., N-I point: 150.0° C.

EXAMPLES 2-65

Example 1 was repeated except that trans-4-(trans-4'-propylcyclohexyl)cyclohexanecarboxylic acid chloride in Example 1 was converted into the corresponding various carboxylic acid chlorides, and besides 2-cyano-4-fluorophenol, 2-cyano-4-chlorophenol in place of 2-cyano-4-fluorophenol was used, to obtain other compounds of the formula (I). The phase transition points of these compounds are shown in Table 1 (compounds of the formula (IV)), Table 2 (compounds of the formula (II)), Table 3 (compounds of the formula (III)) and Table 4 (compounds of the formula (V)).

TABLE 1

Phase transition points of compounds of formula (IV)

| Example | R | In formula IV B | In formula IV A | X | C—N point (m.p.) | N—I point |
|---|---|---|---|---|---|---|
| 1 | $C_3H_7$ | cyclohexyl | cyclohexyl | F | 108.7 | 150.0 |
| 2 | $C_2H_5$ | " | " | F | 109.8 | 117.0 |
| 3 | $C_4H_9$ | " | " | F | 114.8 | 148.6 |
| 4 | $C_5H_{11}$ | " | " | F | 117.6 | 152.1 |
| 5 | $C_7H_{15}$ | " | " | F | 109.6 | 143.4 |
| 6 | $C_2H_5$ | " | phenyl | F | 81.3 | (53.9) |
| 7 | $C_3H_7$ | " | " | F | 93.5 | (92.5) |
| 8 | $C_4H_9$ | " | " | F | 67.2 | 93.0 |
| 9 | $C_5H_{11}$ | " | " | F | 85.6 | 105.6 |
| 10 | $C_7H_{15}$ | " | " | F | 82.9 | 104.0 |
| 11 | $C_5H_{11}$ | phenyl | cyclohexyl | F | 76.7 | (28.8) |
| 12 | $C_2H_5$ | cyclohexyl | | Cl | 91.3 | 149.9 |
| 13 | $C_3H_7$ | " | " | Cl | 103.4 | 180.4 |
| 14 | $C_4H_9$ | " | " | Cl | 90.6 | 176.7 |
| 15 | $C_5H_{11}$ | " | " | Cl | 101.8 | 178.7 |
| 16 | $C_5H_{11}$ | " | phenyl | Cl | 71.8 | (60.6) |
| 17 | $C_3H_7$ | cyclohexyl | phenyl | Cl | 113.6 | 127.3 |
| 18 | $C_5H_{11}$ | " | " | Cl | 100.0 | 129.0 |
| 19 | $C_7H_{15}$ | " | " | Cl | 98.1 | 127.0 |

Note: Numeral values in the parentheses represent monotropic liquid crystals.

TABLE 2

Phase transition points of compounds of formula (II)

| Example | R | In formula (II) A | X | C—I point (m.p.) |
|---|---|---|---|---|
| 20 | $C_2H_5$ | cyclohexyl | F | 71.0 |
| 21 | $C_3H_7$ | " | F | 72.8 |
| 22 | $C_4H_9$ | " | F | 80.9 |
| 23 | $C_5H_{11}$ | " | F | 72.1 |
| 24 | $C_6H_{13}$ | " | F | 86.3 |
| 25 | $C_7H_{15}$ | " | F | 79.6 |
| 26 | $C_3H_7$ | phenyl | F | 58.6 |
| 27 | $C_4H_9$ | " | F | 28.4 |
| 28 | $C_5H_{11}$ | " | F | 49.0 |
| 29 | $C_7H_{15}$ | " | F | 48.6 |
| 30 | $C_2H_5$ | cyclohexyl | Cl | 45.5 |
| 31 | $C_3H_7$ | " | Cl | 54.9 |
| 32 | $C_4H_9$ | " | Cl | 55.6 |
| 33 | $C_5H_{11}$ | " | Cl | 55.9 |
| 34 | $C_6H_{13}$ | " | Cl | 67.0 |
| 35 | $C_7H_{15}$ | " | Cl | 63.4 |
| 36 | $C_8H_{17}$ | " | Cl | 72.3 |
| 37 | $C_2H_5$ | phenyl | Cl | 79.6 |
| 38 | $C_4H_9$ | " | Cl | 35.9 |
| 39 | $C_5H_{11}$ | " | Cl | 51.6 |
| 40 | $C_7H_{15}$ | " | Cl | 62.0 |
| 41 | $C_8H_{17}$ | " | Cl | 60.1 |
| 42 | $C_2H_5O$ | " | Cl | 177.5 |
| 42 | $C_3H_7O$ | " | Cl | 108.9 |
| 44 | $C_4H_9O$ | " | Cl | 85.9 |

TABLE 2-continued

Phase transition points of compounds of formula (II)

| Example | R | In formula (II) A | X | Phase transition point (°C.) C—I point (m.p.) |
|---|---|---|---|---|
| 45 | $C_5H_{11}O$ | " | Cl | 70.8 |
| 46 | $C_6H_{13}O$ | " | Cl | 90.0 |
| 47 | $C_7H_{15}O$ | " | Cl | 74.7 |

TABLE 3

Phase transition points of compounds of formula (III)

| | In formula (III) | | | Phase transition point (°C.) C—I point |
|---|---|---|---|---|
| Example | R | X | Z | Y | (m.p.) |
| 48 | $C_5H_{11}O$ | F | Cl | H | 122.0 |
| 49 | $CH_3$ | F | F | H | 135.2 |
| 50 | $C_5H_{11}O$ | Cl | Cl | H | 120.0 |
| 51 | $CH_3$ | Cl | F | H | 152.8 |
| 52 | $CH_3O$ | Cl | Cl | H | 186.8 |
| 53 | $C_5H_{11}O$ | Cl | H | Cl | 96.1 |
| 54 | $C_3H_7O$ | Cl | H | Cl | 117.2 |
| 55 | $C_5H_{11}O$ | F | H | Cl | 101.9 |

EXAMPLE 66 (USE EXAMPLE 1)

A nematic liquid crystal composition of esters A consisting of

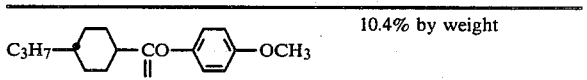

10.4% by weight

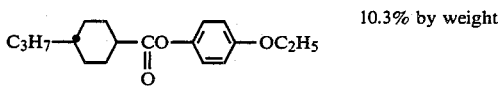

10.3% by weight

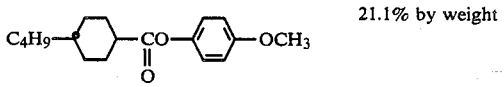

21.1% by weight

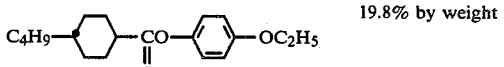

19.8% by weight

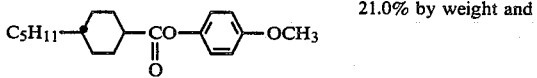

21.0% by weight and

TABLE 4

Phase transition points of compounds of formula (V)

| | | In formula (V) | | | | Phase transition point (°C.) | | |
|---|---|---|---|---|---|---|---|---|
| Example | R | C | B | A | X | C—S point or C—N point | S—N point | N—I point |
| 56 | $C_5H_{11}$ | benzene | benzene | benzene | F | 167.0 | 173.4 | 274.5 |
| 57 | " | " | " | " | Cl | 157.6 | 159.2 | 284.1 |
| 58 | " | cyclohexane | " | " | F | 93.8 | — | 266.0 |
| 59 | " | " | " | " | Cl | 105.2 | — | 274.5 |
| 60 | " | " | cyclohexane | " | F | 118.0 | — | 231.6 |
| 61 | " | " | " | " | Cl | 106.8 | — | 214.0 |
| 62 | $C_3H_7$ | " | cyclohexane+benzene | " | F | 112.9 | — | 203.7 |
| 63 | " | " | " | " | Cl | 130.1 | — | 247.0 |
| 64 | " | " | " | cyclohexane | F | 190.4 | — | 246.0 |
| 65 | " | " | " | " | Cl | 160.5 | — | 267.0 |

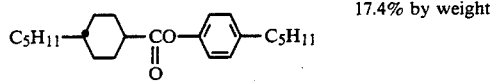

17.4% by weight has a N-I point of 62.8° C., a Δε of −1.0 and a viscosity at 20° C. of 18.5 cp. A commercially available dyestuff (G-224, made by Mercke Co.) (1%) was added to the composition A, and the mixture was sealed in a cell to prepare a liquid crystal cell of guest-host type, followed by measuring its threshold voltage to give a value of 3.80 V. Next, to the above liquid crystal composition A (75 parts by weight) were added trans-4-propylcyclohexanecarboxylic acid-2-cyano-4-fluorophenyl ester (compound of Example 21 of the present invention) (5 parts by weight), trans-4-butylcyclohexanecarboxylic acid-2-cyano-4-fluorophenyl ester (compound of Example 22) (5 parts by weight) and trans-4-pentylcyclohexanecarboxylic acid-2-cyano-4-fluorophenyl ester (compound of Example 23) (5 parts by weight) to prepare a liquid crystal composition, which had a N-I point of 47° C., a Δε of −2.7 and a density at 20° C. of 24.7 cp. To this composition was added the same dyestuff G-224 (1%) as above to prepare a liquid crystal cell of guest-host type, the threshold voltage of which was then measured to give a notably reduced value of 3.10.

EXAMPLE 67 (USE EXAMPLE 2)

To the nematic liquid crystal composition A (80 parts by weight) were added trans-4-heptylcyclohexanecarboxylic acid-2-cyano-4-chlorophenyl ester of Example 35 (a compound of the present invention) (10 parts by weight) and trans-4-(trans-4'-propylcyclohexyl)cyclohexanecarboxylic acid-2-cyano-4-chlorophenyl ester of Example 13 (10 parts by weight) to prepare a liquid crystal composition, which had a N-I point of 68° C., a Δε of −4.0 and a viscosity at 20° C. of 25.5 cp. The same dyestuff G-224 as above (1%) was added to the composition. Using the resulting composition, a guest-host type liquid crystal cell was prepared, and its threshold voltage was measured to give a notably reduced value of 3.20 V.

EXAMPLE 68 (USE EXAMPLE 3)

2-Chloro-4-pentyloxybenzoic acid-2-cyano-4-chlorophenyl ester of Example 50 (a compound of the present invention) (10 parts by weight) was blended with the above-mentioned nematic liquid crystal composition A (90 parts by weight) to prepare a liquid crystal composition, which had a N-I point of 34.5° C., a Δε of −1.2 and a viscosity at 20° C. of 28.5 cp. The same dyestuff G-224 as above (1%) was added to the composition. Using the resulting composition, a guest-host type liquid crystal cell was prepared, and its threshold voltage was measured to give a notably reduced value of 3.26 V.

EXAMPLE 69 (USE EXAMPLE 4)

An ester nematic liquid crystal composition B consisting of

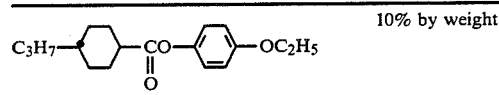

10% by weight

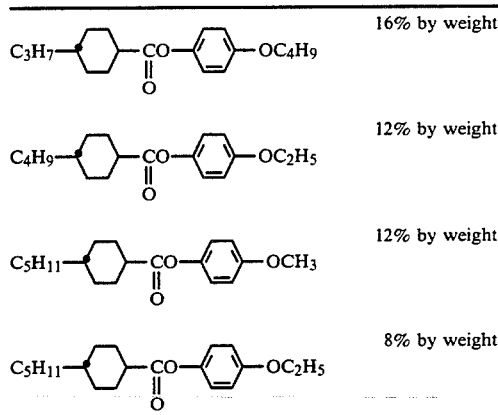

has a N-I point of 74.5° C., a dielectric anisotropy value Δε of −1.4 and a viscosity at 20° C. of 20.3 cp. To this composition was added the same dyestuff G-224 as above (1%) and the mixture was sealed in a cell to prepare a guest-host cell, followed by measuring its threshold voltage to give a value of 3.7 V. Next, trans-4-(trans-4'-propylcyclohexyl)cyclohexanecarboxylic acid-2-cyano-4-fluorophenyl ester of Example 1 (a compound of the present invention) (5 parts by weight), trans-4-(trans-4'-butylcyclohexyl)cyclohexanecarboxylic acid-2-cyano-4-fluorophenyl ester of Example 3 (5 parts by weight) and trans-4-(trans-4'-pentylcyclohexyl)cyclohexanecarboxylic acid-2-cyano-4-fluorophenyl ester of Example 4 (5 parts by weight) were added to the above liquid crystal composition B (75 parts by weight) to prepare a liquid crystal composition, which had a N-I point of 79.2° C., a dielectric anisotropy Δε of −2.4 and a viscosity at 20° C. of 27 cp. To this composition was added the same dyestuff G-224 as above (1%), followed by measuring its threshold voltage to give a notably reduced value of 2.9 V.

EXAMPLE 70 (USE EXAMPLE 5)

To the above-mentioned nematic liquid crystal composition A (85 parts by weight) were added 4-[trans-4-(trans-4-propylcyclohexyl)cyclohexyl]benzoic acid-2-cyano-4-chlorophenyl ester of Example 63 (10 parts by weight) and trans-4''-propyl-trans-octadecahydro-p-terphenyl-trans-4-carboxylic acid-2-cyano-4-chlorophenyl ester of Example 65 (5 parts by weight) to prepare a liquid crystal composition, which had a N-I point of 32.3° C., a Δε of −1.2 and a viscosity at 20° C. of 30.0 cp. To the composition was added the same dyestuff G-224 (1% by weight) as above, to prepare a guest-host cell the threshold voltage of which was measured to give a notably reduced value of 3.20 V.

EXAMPLE 71 (USE EXAMPLE 6)

To the above nematic liquid crystal composition A (85 parts by weight) were added 4-(trans-4-pentylcyclohexyl)biphenylyl-4'-carboxylic acid-2-cyano-4-fluorophenyl ester of Example 62 (a compound of the present invention) (5 parts by weight), trans-4-[4-(trans-4-pentylcyclohexyl)phenyl]cyclohexanecarboxylic acid-2-cyano-4-fluorophenyl ester of Example 60 (5 parts by weight) and trans-4-[4-(trans-4-pentylcyclohexyl)phenyl]cyclohexanecarboxylic acid-2-cyano-4-chlorophenyl ester of Example 63 (5 parts by weight), to prepare a liquid crystal composition, which had a N-I point of 83.4° C., a Δε of −1.2 and a viscosity at 20° C. of 30.3 cp. To this composition was added the same dyestuff G-224 as above (1 wt.%) and the mixture was sealed in the same cell as above to prepare a guest-host type liquid crystal cell the threshold voltage of which was measured to give a notably reduced value of 3.26 V.

What we claim is:

1. The 2-cyano-4-halogenophenyl esters expressed by the formula:

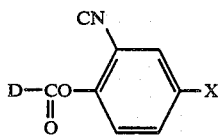

wherein D is selected from the group consisting of

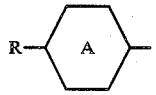 (1)

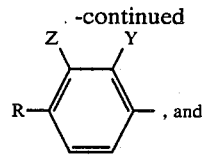 (2)

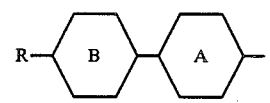 (3)

wherein R represents hydrogen atom or an alkyl group or an alkoxy group of 1 to 10 carbon atoms;

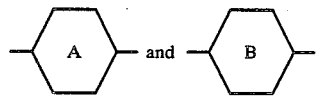

each represent either one of

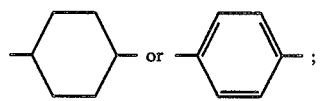

X represents F or Cl; and Y and Z each represent a hydrogen atom or F or Cl.

* * * * *